(12) United States Patent
Yin et al.

(10) Patent No.: US 10,512,605 B2
(45) Date of Patent: Dec. 24, 2019

(54) INTEGRATED NANO SYSTEM FOR LIVER-TARGETING CO-DELIVERY OF GENES/DRUGS AND PREPARATION METHOD

(71) Applicants: Jiangnan University, Wuxi (CN); Max Planck Institute of Colloids and Interfaces, Potsdam (DE)

(72) Inventors: Jian Yin, Wuxi (CN); Jing Hu, Wuxi (CN); Peter Seeberger, Potsdam (DE); Zhou Ye, Wuxi (CN)

(73) Assignees: Jiangnan University, Wuxi, Jiangsu (CN); Max Planck Institute of Colloids and Interfaces, Potsdam (DE)

( * ) Notice: Subject to any disclaimer, the term of this patent is extended or adjusted under 35 U.S.C. 154(b) by 0 days.

(21) Appl. No.: 16/215,395

(22) Filed: Dec. 10, 2018

(65) Prior Publication Data
US 2019/0160007 A1    May 30, 2019

Related U.S. Application Data

(63) Continuation of application No. PCT/CN2017/116185, filed on Dec. 14, 2017.

(30) Foreign Application Priority Data

Nov. 30, 2017 (CN) .......................... 2017 1 1235718

(51) Int. Cl.
| | | |
|---|---|---|
| *A61K 47/26* | (2006.01) | |
| *A61K 9/107* | (2006.01) | |
| *A61K 47/32* | (2006.01) | |
| *A61K 49/00* | (2006.01) | |
| *C12N 15/113* | (2010.01) | |
| *A61K 31/7088* | (2006.01) | |
| *A61P 35/00* | (2006.01) | |
| *A61K 31/65* | (2006.01) | |

(52) U.S. Cl.
CPC ............ *A61K 9/1075* (2013.01); *A61K 31/65* (2013.01); *A61K 31/7088* (2013.01); *A61K 47/26* (2013.01); *A61K 47/32* (2013.01); *A61K 49/0041* (2013.01); *A61K 49/0082* (2013.01); *A61P 35/00* (2018.01); *C12N 15/113* (2013.01); *C12N 2310/14* (2013.01); *C12N 2320/32* (2013.01)

(58) Field of Classification Search
None
See application file for complete search history.

(56) References Cited

FOREIGN PATENT DOCUMENTS

| CN | 101259284 A | 9/2008 |
|---|---|---|
| CN | 108066285 A | 5/2018 |

OTHER PUBLICATIONS

Qian, X. M. et al., Star-branched Amphiphilic PLA-b-PDMAEMA Copolymers for Co-delivery of MiR-21 Inhibitor and Doxorubicin to Treat Glioma, Biomaterials, Dec. 12, 2013(Dec. 12, 2013), vol. 35, pp. 2322-2335.
Sun P. F. et al., A Water-soluble Phosphorescent Conjugated Polymer Brush for Tumor-targeted Photodynamic Therapy, Polymer Chemistry, Oct. 14, 2017(Oct. 14, 2017), vol. 8, pp. 5836-5844.
Zhou Ye et al., An Integrated Therapeutic Delivery System for Enhanced Treatment of Hepatocellular Carcinoma, Advanced Functional Materials, Mar. 12, 2018(Mar. 12, 2018), No. 28, pp. 1-13.

*Primary Examiner* — James W Rogers
(74) *Attorney, Agent, or Firm* — IPro, PLLC; Na Xu

(57) ABSTRACT

The present disclosure discloses an integrated nano system for liver-targeting co-delivery of genes/drugs and a preparation method, belonging to the field of biomedicines. In the disclosure, a plurality of functions are integrated in a carrier having good biocompatibility and safety, a nucleic acid/drug-loading copolymer portion having a pH-stimulating response function is formed by poly(N,N-dimethylaminoethyl methacrylate) (PDMAEMA) grafted with poly(3-azido-2-hydroxypropylmethacrylate) (PGMA-N3), and a fluorescence-based imaging component Rhodamine B (RhB) and galactose are used as targeting ligands. The drug delivery system provided by the present disclosure is safe, is capable of taking a synergistic effect of gene/drug therapy, and is expected to play a great role in clinical application.

9 Claims, 6 Drawing Sheets

INTEGRATED NANO SYSTEM FOR LIVER-TARGETING CO-DELIVERY OF GENES/DRUGS AND PREPARATION METHOD

TECHNICAL FIELD

The present disclosure relates to an integrated nano system for a liver-targeting co-delivery of genes/drugs and a preparation method, and particularly relates to a copolymer nano micelle having liver tumor tissue targeting property and tracing property and capable of loading nucleic acid substances and drugs, belonging to the field of biomedicines.

BACKGROUND

For decades, liver cancer is always the second most common main cause of death induced by cancer all over the world, and there are about 750 thousand new cases each year. Furthermore, morbidity and mortality of liver cancer have a tendency to increase year by year, and health and life of Chinese and even global people are seriously threatened. High incidence of morbidity and mortality of liver cancer mainly attribute to later diagnosis and limited available treatment methods for the disease. In addition, surgical treatment is not suitable for most of patients due to lack of available transplantation donors. Thus, it is urgent to develop a new liver cancer treatment strategy. Prosperous development of a nano technology can well overcome disadvantages existing in the current liver cancer treatment. Since physical and chemical properties of the nano material can be precisely improved through regulation of chemical components, size, shape, structure, morphology, surface modification and the like, the nano material can be used as a potential carrier for co-delivery of nucleic acid substances and drugs to be used for liver cancer treatment. However, due to the defects of immunogenicity, low transfection efficiency, toxic or side effects and the like of the present nano material, its development of clinical application is hindered. In addition, due to complexity of intrahepatic and extrahepatic metastasis of liver cancer, the present nano material for liver cancer treatment is far from enough in the aspect of study on an in vivo treatment effect in a subcutaneous solid tumor mouse model.

In recent years, a cationic polymer poly(N,N-dimethylaminoethyl methacrylate) (PDMAEMA) has been largely used as a stable complex formed by loading nucleic acid with negative charges to be used for gene therapy as containing a large amount of amino groups. Under the acidic condition, a sponge effect can be triggered to cause escape of an inclusion body, so as to perform gene transfection. Moreover, this polymer can easily form a copolymer with other hydrophobic fragments via a free radical polymerization technology, and the hydrophobic drug is coated in the hydrophobic fragments through hydrophilic and hydrophobic interaction. These advantages allow combination of PDMAEMA and other polymers to become an ideal carrier for achieving co-delivery of nucleic acid for liver cancer treatment and an anti-cancer drug. For liver-targeting recognition, the ligand, since the surfaces of liver cells are overexpressed with an asialoglycoprotein receptor (ASGPR), can be specifically recognized, thereby reducing toxic or side effects. Because of low price, wide source, easy modification and other features, galactose has been widely used for modifying nano materials and applied to study on in vitro and in vivo (subcutaneous solid tumor mouse model) antitumor effects of specifically targeted human hepatoma cells. In addition, introduction of a fluorescence label into a nano system can render the nano material to be monitored in real time in vivo, thereby improving the potential for clinical diagnosis and treatment.

Although there have been many related studies for obtaining a nano material capable of achieving co-delivery of nucleic acid and an anti-cancer drug, these systems for liver cancer treatment have not been sufficiently utilized yet. And there is no report about introduction of a tracing molecule and a targeting molecule into a co-delivery carrier of nucleic acid having a stimulating response function and the anti-cancer drug. It is still a challenge that multiple functions are integrated into the same nano carrier to be used for liver cancer targeting treatment.

SUMMARY

The present disclosure provides a novel integral treatment system, which integrates multiple functional fragments to a carrier with good biocompatibility and safety by designing a series of reactions, to solve the difficult problem of integrating multiple functions to the same nanomaterial carrier. Firstly, a fluorescent molecule (for example, Rhodamine B, RhB) having a fluorescence imaging function is modified into a bromine-containing macroinitiator which can trigger free radical polymerization reaction of monomers 3-azido-2-hydroxypropylmethacrylate (GMA-$N_3$) and N,N-dimethylaminoethyl methacrylate (DMAEMA), so as to form a covalently bound polymer with the fluorescent molecule. In this polymer, PGMA-$N_3$ has a function of loading a hydrophobic drug through hydrophilic and hydrophobic interaction, and the PDMAEMA portion can coat nucleic acid substances since it contains a large number of amino groups which can be protonated under the acidic condition to trigger the sponge effect to cause escape of the inclusion body, thereby performing gene transfection and promoting release of the hydrophobic drug. In the other aspect, the galactose terminal group site, which has a liver targeting function, is modified to contain an alkynyl group, and can covalently bind with the azido group of the PGMA-$N_3$ portion of the copolymer, thereby providing a stable targeting function for a carrier. The targeted copolymer can form a nano micelle integrating multiple functions of targeting, tracing, acid sensitivity, loading both drugs and genes and the like through self-assembling.

The biocompatibility and cytotoxicity of the nano system provided by the present disclosure have been seriously assessed, and there have been no reports about the integrated nano micelle designed by the present disclosure so far. Stability of the copolymer nano micelle coloaded both nucleic acid and drugs and drug release triggered by acidic pH are studied in vitro. The study on the synergistic effect of drug delivery, gene transfection and gene/drug therapy is performed in HepG2 and Hub7 cell lines. In addition, in vivo behavior tracing and treatment effect assessment is performed in subcutaneous solid tumor and in-situ tumor mouse models.

Firstly, the present disclosure provides an acid-sensitive tracing polymer nano delivery system for treating liver cancer, which can be used for target treatment of liver diseases in combination with gene therapy and chemotherapy. The delivery system is a compound as shown in Formula 1 below:

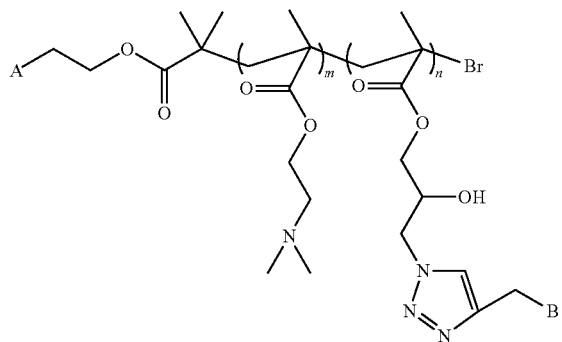

Formula 1 in the above Formula 1,

A is one or more identical or different fluorescent molecules having a fluorescence tracing function selected from, for example, Rhodamine B, isothiocyanate fluoresceine, BODIPY, etc.

B is one or more identical or different monosaccharide or oligosaccharide molecules having galactose or galactosamine residues, which can specifically recognize asialoglycoprotein receptors over-expressed on the surfaces of hepatoma cells;

the Formula 1 contains a monomer structure of N,N-dimethylaminoethyl methacrylate (DMAEMA) and m represents a degree of polymerization, and m=25; and the Formula 1 contains a monomer structure of 3-azido-2-hydroxypropylmethacrylate (GMA-N3), and n represents a degree of polymerization, and n=50.

In an embodiment of the present disclosure, the mole ratio of fluorescent molecule Rhodamine B to DMAEMA to GMA-N3 is 1:25:50, and the ratio of the targeting saccharide molecule to GMA-N3 is 1:1.

The present disclosure also provides a method for preparing the acid-sensitive tracing polymer nano delivery system used for target treatment of liver cancer in combination with gene therapy and chemotherapy, by which tracing molecule Rhodamine B and targeting molecule galactose are respectively introduced into the copolymer through initiator modification and click reaction. The method includes the following steps:

Step 1: preparation of copolymer of interest RhB-PDMAEMA25-c-PGMA50-Gal

The initiator BromoRhodamine B, a monomer DMAEMA and a monomer GMA-N3 are added into a 25mL round-bottom flask in the mole ratio of 1:25:50 dissolved by 2 mL of tetrahydrofuran, and argon is introduced for 30 min to remove the oxygen in the flask, wherein the stabilizer in the monomer EMAEMA needs to be removed in advance, namely, the DMAEMA crude product is enabled to rapidly pass through an alkaline aluminum oxide column. Under the protection of nitrogen, cuprous bromide and pentamethyl diethylenetriamine are added in sequence. The flask is sealed, and the reaction is carried out for 8 h at room temperature under the protection of nitrogen. After reaction is ended, tetrahydrofuran (10mL) is added into reaction solution, the reaction solution in the flask is sufficiently stirred and dissolved. Then the solution passes through a neutral aluminum oxide column to remove a copper ligand in a mixed solution, and the obtained liquid is collected and subjected to rotary evaporation to remove a solvent. Then viscous liquid in the flask is dropwise and slowly added into petroleum ether (500mL) for repeated precipitation for three times, and the obtained precipitant is vacuum-dried to obtain Rhodamine B modified copolymer RhB-PDMAEMA25-c-PGMA50-N3.

Propargyl modified deacetylated galactose and Rhodamine B modified copolymer RhB-PDMAEMA25-c-PGMA50-N3 are dissolved into 5mL of DMF, then copper sulfate and sodium ascorbate are dissolved into 5mL of water and then dropwise added into the above reaction solution. The reaction solution is stirred for 48 h at room temperature. The reaction solution is filtered, and dialyzed in aqueous solution (dialysis bag molecular cut off: 8-10 kDa) to obtain the copolymer of interest RhB-PDMAEMA25-c-PGMA50-Gal.

Step 2: preparation of target therapy system micelle Ga-micelles

1) The copolymer of interest RhB-PDMAEMA25-c-PGMA50-Gal in step 1 is dissolved with DMSO, and stirred for 5 h;

2) dialysis is carried out for 48 h in double distilled water, and water is changed once every 6 hours to prepare micelle solution; and 3) the micelle solution is lyophilized via a freezer dryer to prepare the micelle Gal-micelles.

Step 3: preparation of drug-loading target therapy system micelle DOX@Gal-micelles 1) The copolymer of interest in Step 1 and a drug are dissolved respectively with DMSO, and the two solutions are mixed and stirred for 5 h;

2) the mixed solution is dialyzed for 48 h in double distilled water, and water is changed once every 6 hours to prepare drug-loading micelle solution; and 3) the polymer micelle solution is enabled to pass through a 0.45 μm micromembrane to be filtered to remove the unloaded drug, and then is lyophilized via a freezer dryer to prepare the drug-loading micelle DOX@Gal-micelles.

Step 4: preparation of gene therapy system micelle loading both plasmid DNA (pGFP) and the drug, namely DOX@Gal-micelles/pGFP The drug-loading DOX@Gal-micelles in step 3 is dissolved into PBS buffer, and plasmid pGFP is diluted into stock solution using double distilled water. The complex of the copolymer and DNA is prepared according to the mole ratio of the content of nitrogen in a monomer DMAEMA in the copolymer to the content of phosphorus in nucleic acid of 30:1. The stock solution and the complex are evenly mixed, and stand for 30 min at room temperature to obtain the copolymer micelle loading both nucleic acid and the drug, namely DOX@Gal-micelles/pGFP.

Step 5: preparation of target therapy system micelle loading both small molecule siRNA (Bcl-2 siRNA) and the drug, namely DOX@Gal-micelles/siRNA The drug-loading DOX@Gal-micelles in step 3 is dissolved into PBS buffer, and small molecule siRNA (Bcl-2 siRNA) is diluted into stock solution using double distilled water. A complex of the copolymer and RNA is prepared according to a mole ratio of the content of nitrogen in a monomer DMAEMA in the copolymer to the content of phosphorus in nucleic acid of 30:1; and the stock solution and the complex are evenly mixed, and stand for 30 min at room temperature to obtain the copolymer micelle loading both nucleic acid and the drug, namely, DOX@Gal-micelles/siRNA.

In an embodiment of the present disclosure, the mole ratio of the Rhodamine B initiator in step 1 to the DMAEMA monomer structure unit to 3-azido-2-hydroxyl propyl methacrylate input material is 1:25:50.

In an embodiment of the present disclosure, the mole ratio of the Rhodamine B initiator in step 1 to cuprous bromide to N,N,N',N',N"-pentamethyl diethylenetriamine for reaction is 1:1:1.

In an embodiment of the present disclosure, the average particle size of the nano micelle formed in Step 2 is 155 nm.

In an embodiment of the present disclosure, the concentration of the copolymer in Step 2 is 10-50 mg/mL.

In an embodiment of the present disclosure, the amount of DMSO of the copolymer in Step 2 is 0.5-1 mL.

In an embodiment of the present disclosure, in Step 3, the concentration of the copolymer is 10-50 mg/mL.

In an embodiment of the present disclosure, in Step 3, the concentration of adriamycin is 2-10 mg/mL.

In an embodiment of the present disclosure, the amount of DMSO of the copolymer in Step 3 is 0.5-1 mL.

In an embodiment of the present disclosure, in Step 4, the concentration of the drug-loading copolymer is about 3.5 mg/mL.

In an embodiment of the present disclosure, in Step 4, the concentration of small molecule RNA is about 20 μg/mL.

The present disclosure also relates to application of the acid-sensitive tracing polymer nano delivery system for target treatment of liver cancer in combination with gene therapy and chemotherapy. Particularly, chemotherapeutic drugs are an anti-cancer drug or an anti-tumor drug. More particularly, the anti-cancer drug is adriamycin.

The present disclosure also relates to application of the acid-sensitive tracing polymer nano delivery system for target treatment of liver cancer in combination with gene therapy and chemotherapy. Particularly, nucleic acid adopted in gene therapy is plasmid DNA or small molecule siRNA. More particularly, the nucleic acid substance is pGF or Bcl-2 siRNA.

In the acid-sensitive tracing polymer nano delivery system for target treatment of liver cancer in combination with gene therapy and chemotherapy provided by the present disclosure, the monomer GMA is to provide a hydrophobic portion to interact with the hydrophobic anti-cancer drug adriamycin to coat the adriamycin in its hydrophobic core; and the monomer DMAEMA is to, on the one hand, provide a hydrophilic portion, and on the other hand, to coat small molecule nucleic acid with negative charges therein through static interaction. Through regulation of the ratio of the monomer DMAMEA to GMA-N3, the size of the formed nano micelle can be regulated to achieve the effects of controlling drug loading capacity and encapsulation efficiency. The outer layer of nano micelle is a monosaccharide or oligosaccharide molecule, so that the micelle has good biocompatibility. And thses molecules have good targeting property, which can carry the anti-cancer drug and genes to pass through cytomembrane, and even through the nuclear membrane to enter the cell nucleus, and can be used as a carrier of various drugs and nucleic acid.

The acid-sensitive tracing polymer nano delivery system for target treatment of liver cancer in combination with gene therapy and chemotherapy and the preparation method thereof provided by the present disclosure have the following beneficial effects:

(1) The delivery system DOX@Gal-micelles/siRNA of the present disclosure can be stably present in the process of delivery (pH7.4), and is capable of effectively reducing drug leakage; and, under an acidic pH environment, drug release can be accelerated, and the release amount of the drug is improved.

(2) The delivery system of the present disclosure can promote in vivo and in vitro real-time imaging as containing the covalently bound Rhodamine B molecule.

(3) The delivery system of the present disclosure can target asialoglycoprotein receptors (ASGPR) over-expressed on the surfaces of hepatoma cells as containing the covalently bound galactose molecule, thereby achieving the purpose of target delivery.

(4) The delivery system of the present disclosure can take a synergistic effect in a subcutaneous solid tumor mouse model and an in situ tumor mouse model through co-delivery of nucleic acid substances and anti-cancer drugs, thereby improving anti-cancer efficiency.

The acid-sensitive tracing polymer nano delivery system for target treatment of liver cancer in combination with gene therapy and chemotherapy synthesized by the present disclosure has low cytotoxicity. Under the experimental conditions, different proportions of copolymer micelles are jointly incubated with human hepatoma cells HepG2 and Hub7 cells and human embryonic kidney cells HEK293 cells for 48 h at different concentrations, and all the cell survival rates are more than 80% at the concentration up to 400 μg/mL. Moreover, the gene/drug-loading micelle whose surface is bound with galactose has high cytomembrane passing ability, and even is capable of passing through the nucleic membrane to enter a cell nucleus. Through fluorescence confocal microscopy test and flow cytometry analysis, it is demonstrated that the nucleic acid/drug-loading copolymer micelle whose surface is bound with the galactose molecule can be endocytosed by HepG2 and Hub7 cells which has over-expressed asialoglycoprotein receptor on the surface of the cytomembrane, while only a few of micelles can be endocytosed by HEK293 cells of low-expressed asialoglycoprotein receptor on the surface of the cytomembrane, indicating that the micelle has targeting property on a specific cancer cell or tissue. Through in vivo study on the subcutaneous solid tumor mouse model and the in situ tumor mouse model, it is proved that the micelle has high in vivo anti-cancer efficiency.

DETAILED DESCRIPTION

Figure 1:
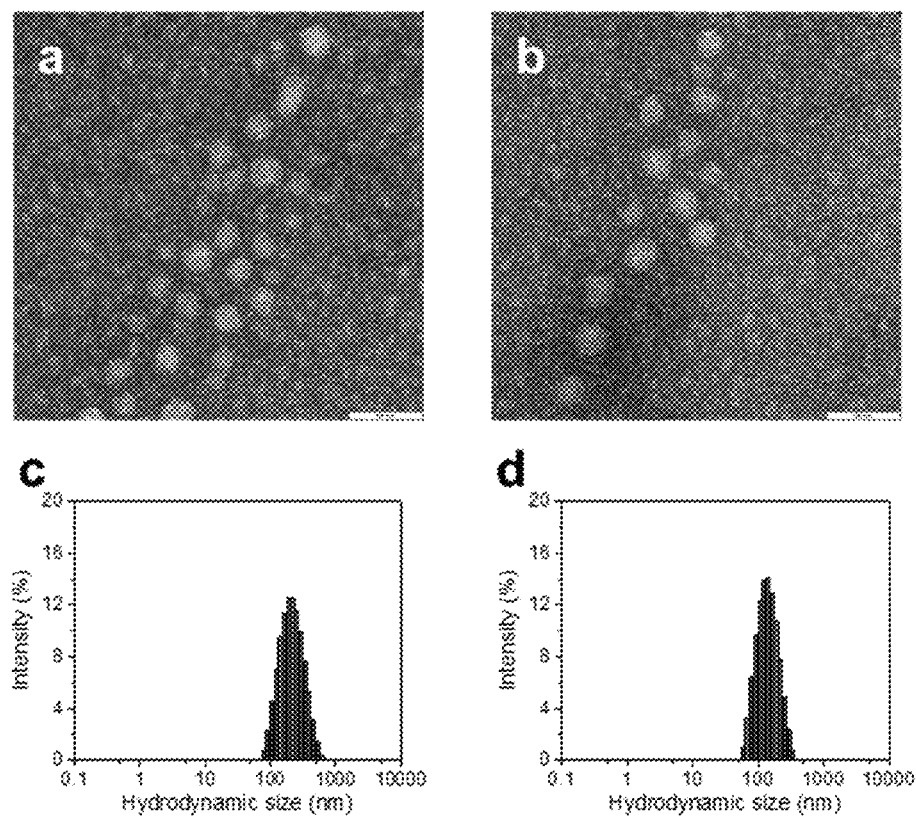
FIG. 1: particle size distribution of copolymer micelle Gal-micelles and nucleic acid/drug-loading micelle DOX@Gal-micelles/pGFP. a) a transmission electron microscope graph of copolymer micelle Gal-micelles; b) a transmission electron microscope graph of nucleic acid/drug-loading micelle DOX@Gal-micelles/pGFP; c) a dynamic light scattering particle size distribution graph of copolymer micelle Gal-micelles; and d) a dynamic light scattering particle size distribution graph of copolymer micelle Gal-micelles.

Next, embodiments of the present disclosure will be described in detail in conjunction with Embodiments, those skilled in the art will understand that the following Embodiments are only for illustrating the present disclosure but not considered as defining the scope of the present disclosure. If specific conditions are not noted in Embodiments, these Embodiments are performed according to conventional conditions or manufacturer's recommendation conditions. If manufacturers of used agents or instruments are not noted, all the agents or instruments are commercially available conventional products.

Embodiment 1: Preparation of Bromo-Rhodamine B Initiator 15.52 g (25.00 mmol) of glycol and 1.01 g (10.00 mmol) of triethylamine are weighed and placed in a 100 mL conical flask to be stirred, and ice-water bath is carried out to 0° C., and then 1.20 mL (10.00 mmol) of 2-bromoisobutyryl bromide is dropwise added in nitrogen atmosphere. Then, the temperature is slowly raised to room temperature, and magnetic stirring is carried out for 3 h. 100 mL of deionized water is added into reacted solution for quenching, and extraction is carried out with dichloromethane (100 mL×3). The collected organic phase is extracted with deionized water (100 mL×3). A proper amount of anhydrous magnesium sulfate is added in the extracted organic phase, and drying is carried out for 12 h. The oily crude product is obtained by spin distillation after filtration, and a colorless and sticky product hydroxyethyl bromoisobutyrate is obtained by reduced pressure distillation (85° C., 30 mTorr).

4.81 g (10.00 mmol) of Rhodamine B, 2.90 g (15.00 mmol) of 1-ethyl-(3-dimethylaminopropyl) carbonyl diimine hydrochloride and 3.22 g (15.00 mmol) of compound hydroxyethyl bromoisobutyrate are weighted and dissolved into 40 mL of anhydrous dichloromethane to be stirred, and ice-water bath is carried out to 0° C. Then 1.82 g (15 μmol) of 4-dimethylaminopyridine is added, and then the temperature is slowly raised to room temperature and react for 12 h. Reaction solution is extracted with 0.1 M HCl (50 mL×3) and then washed for three times respectively with saturated sodium bicarbonate solution and saturated salt solution. The organic phase is dried with anhydrous magnesium sulfate and filtered, and then the solvent is removed by spin distillation. And the bromo-Rhodamine B initiator is obtained by separation on a silica gel column (a volume ratio of eluent to dichloromethane/methanol is 10:1). The specific method can refer to a document (Marcromolecules, 2011, 44, 2050-2057).

Embodiment 2: Preparation of 3-Azido-2-Hydroxypropyl Methacrylate GMA-N3

3.71 g (57.00 mmol) of sodium azide and 3.81 g (45.20 mmol) of sodium bicarbonate are dissolved into 60mL of tetrahydrofuran/water (5:1v/v) and stirred. Then 5.42 g (37.80 mmol) of glycidyl methacrylate is slowly added to the mixture to react for 48 h at room temperature. The solvent is removed by spin distillation after insoluble salt substances are filtered out, and the obtained concentrate is extracted twice with dichloromethane. Then the obtained organic phase is dried with anhydrous magnesium sulfate and filtered, and the solvent is removed by spin distillation. Then 3-azido-2-hydroxypropyl methacrylate is obtained by separation on a silica gel column (a volume ratio of eluent to n-hexane/ethyl acetate is 9:1). A specific method can refer to a document (Polymer Chemistry, 2015, 6, 3875-3884; Soft Matter, 2009, 5, 4788-4796).

Embodiment 3: Preparation of Rhodamine B Modified Copolymer (RhB-PDMAEMA25-c-PGMA50-N$_3$)

70.0 g (0.10 mmol) of the initiator bromo-Rhodamine B, 484.0 mg (2.75 mmol) of monomer DMAEMA and 1.01 g (5.50 mmol) of compound 3-azido-2-hydroxypropyl methacrylate are correctly weighed and added into a 25mL round-bottom flask and dissolved with 2 mL of tetrahydrofuran. Then the argon is introduced for 30 min to remove oxygen in the flask, wherein, the stabilizer in the monomer DMAEMA needs to be removed in advance, namely, the DMAEMA crude product is enabled to rapidly pass through an alkaline alumina column. 18.9 mg (0.10 mmol) of CuBr and PMDETA (28 μL, 0.10 mmol) are added in turn under the protection of nitrogen. Then the flask is sealed, and reaction is carried out for 8 h at room temperature under the protection of nitrogen. After the reaction is ended, tetrahydrofuran (10 mL) is added into reaction solution. The reaction solution in the flask is sufficiently stirred, and then passes through a neutral alumina column to remove a copper ligand in the mixed solution. The obtained liquid is collected and the solvent is removed by spin distillation, then sticky liquid in the flask is dropwise and slowly added into petroleum ether (500 mL) for repeated precipitation for three times. The obtained precipitate is vacuum-dried to obtain Rhodamine B modified copolymer RhB-PDMAEMA25-c-PGMA50-$N_3$.

For other proportions of copolymers, different concentrations of monomers DMAEMA are respectively added at the starting of reaction to obtain copolymer RhB-PDMAEMA-c-PGMA-$N_3$ having different proportions of monomers, including RhB-PDMAEMA10-c-PGMA50-$N_3$ and RhB-PDMAEMA50-c-PGMA50-$N_3$.

Embodiment 4: Preparation of Propargyl-Modified Deacetylated Galactose 6.21g (15.90 mmol) of peracetyl galactose is dissolved into 75 mL of anhydrous dichloromethane, and then 1.0 mL (18.00 mmol) of propargyl alcohol is added. Cooling is carried out to 0° C. and stirring is carried out for 5 min. Then 3.0 mL (24.30 mmol) of boron trifluoride etherate is dropwise added within 15 min. Stirring is continued at 0° C. for 10 min, and then reaction is carried out for 10 h at room temperature. The reaction is ended by saturated potassium carbonate solution. Then the organic phase is extracted with dichloromethane and washed for three times with saturated salt solution. The organic phase is dried with anhydrous magnesium sulfate and filtered, and the solvent is removed by spin distillation, so propargyl-modified peracetyl galactose is obtained.

2.01 g (5.20 mmol) of propargyl-modified peracetyl galactose is dissolved into 50 mL of 0.30 mol/L methanol solution of sodium methoxide to react at room temperature. Point panel detection is carried out until raw materials disappear. Then $H^+$ exchange resin is added to adjust the reaction solution to be neutral, and filtration is carried out. Then then solvent is removed by spin distillation, and propargyl-modified deacetylated galactose is obtained by separation on a silica gel column (a volume ratio of dichloromethane to methanol is 10:1). A specific method can refer to a document (Bioconjugate Chemistry, 2012, 23, 1166-1173).

Embodiment 5: Preparation of Galactose Modified Copolymer RhB-PDMAEMA25-c-PGMA50-Gal 350.0 g of propargyl-modified deacetylated galactose in Embodiment 4 and 200.1 mg of Rhodamine B modified copolymer RhB-PDMAEMA25-c-PGMA50-$N_3$ in Embodiment 3 are dissolved into 5 mL of DMF, then 98.0 mg (0.61 mmol) of copper sulfate and 242.0 mg (12 mmol) of sodium ascorbate are dissolved into 5 mL of water to be further dropwise added into the above reaction solution. And the reaction solution is stirred for 48 h at room temperature. The reaction solution is filtered and then dialyzed in aqueous solution (dialysis bag molecular cut off: 8-10 kDa), and then the copolymer of interest RhB-PDMAEMA25-c-PGMA50-Gal is obtained.

Embodiment 6: Preparation of Copolymer RhB-PDMAEMA-c-PGMA-Gal in Other Different Proportions The copolymers RhB-PDMAEMA-c-PGMA-$N_3$ having different proportions of monomers obtained in Embodiment 3 replace RhB-PDMAEMA25-c-PGMA50-$N_3$ in Embodiment 5, and other operations are the same as those in Embodiment 5, so as to obtain Rhodamine B modified galactose residue-containing copolymer RhB-PDMAEMA-c-PGMA-Gal having different proportions of monomers, including RhB-PDMAEMA10-c-PGMA50-Gal and RhB-PDMAEMA50-c-PGMA50-Gal.

Embodiment 7: Preparation of Copolymer Micelle

RhB-PDMAEMA25-c-PGMA50-Gal in Embodiment 5 is dissolved with DMSO and stirred for 5 h. Dialysis is carried out in double distilled water for 48 h, and water is changed once every 6 hours, so as to obtain micelle solution. Then the micelle solution is lyophilized using a freeze-drier to prepare copolymer micelle Gal-micelles.

Embodiment 8: Preparation of Other Micelles

RhB-PDMAEMA-c-PGMA-Gal in Embodiment 6 respectively replaces RhB-PDMAEMA25-c-PGMA50-Gal in Embodiment 7, and other operations are the same as those in Embodiment 7. Corresponding micelles are respectively prepared.

Embodiment 9: Preparation of Drug-Loading Micelle

RhB-PDMAEMA25-c-PGMA50-Gal in Embodiment 5 and the adriamycin hydrochloride standard product are respectively dissolved with DMSO. Then triethylamine is added in adriamycin hydrochloride standard product DMSO solution. Two solutions are mixed and stirred for 5 h. The mixed solution is dialyzed in double distilled water for 48 h, and water is changed once every 6 hours, so as to prepare adriamycin-loading micelle solution.

Later, the polymer micelle solution is filtered through a 0.45 μm membrane to remove unloaded adriamycin, and adriamycin-loading micelle DOX@Gal-micelles is prepared by lyophilization in a freeze-drier.

The prepared micelle is sufficiently dissolved in DMSO. The absorbance of the solution at 483 nm is measured using a microplate reader, and corresponding concentrations of adriamycin in the drug-loading micelle are obtained according to standard curves of adriamycin DMSO solutions.

Drug load of the obtained micelle is equal to adriamycin mass in micelle/micelle mass, and is 12.6±0.03%; encapsulation efficiency is equal to adriamycin mass in micelle/starting administration mass, and is 58.0±3.4%.

Embodiment 10: Preparation of Gene/Drug-Loading Copolymer Micelle

The drug-loading DOX@Gal-micelles in Embodiment 9 is dissolved into PBS buffer (140 mM NaCl, 2.7 mM KCl, 10 Mm $Na_2HPO_4$, 1.8 mM $KH_2PO_4$, pH7.4) to be prepared into 3.5 mg/mL stock solution. Plasmid pGFP or small molecule siRNA (Bcl-2 siRNA) is diluted into 20 μg/mL stock solution with double distilled water. The complex of a copolymer and nucleic acid is prepared according to the mole ratio 30:1 of the content of nitrogen in a monomer DMAEMA in the copolymer and the content of phosphorus in nucleic acid. Based on it, these two solutions are mixed evenly, and then stayed for 30 min at room temperature, so as to obtain copolymer micelle loading both genes and a drug, namely DOX@Gal-micelles/pGFP or DOX@Gal-micelles/siRNA.

Embodiment 11: Characterization of Copolymer Micelle

Particle size distribution of Gal-micelles and DOX@Gal-micelles/pGFP prepared in Embodiments 7, 8 and 10 is measured by a dynamic light scattering technology, and changes in particle sizes before and after gene/drug is loaded are compared.

As shown in FIG. 1, through dynamic light scattering particle size detection, Gal-micelles can form a micelle having a particle size of about 155 nm, and its particle size is still about 155 nm after genes and drugs are loaded. However, neither of RhB-PDMAEMA10-c-PGMA50-Gal nor RhB-PDMAEMA50-c-PGMA50-Gal can form uniform micelles.

Stability is one of the most important properties of a nano carrier. A nano particle applied to the field of biomedicines must be stably dispersed in salt solution or a medium within a certain concentration range. The copolymer nano micelle prepared in this experiment is dispersed in aqueous solution, PBS buffer (pH=7.4) and a medium containing 10% fetal bovine serum to measure the change in its particle size.

There is no distinct particle size change within 7 days, indicating that this copolymer nano micelle has good stability.

Embodiment 12: Cytotoxicity Experiment of Copolymer Micelle Gal-Micelles

The copolymer micelle Gal-micelles in Embodiment 7 is added into culture solution for a cell culture experiment, and the relative survival rate of cells is measured using 3-(4,5-dimethylthiazole-2)-2,5-diphenyltetrazole bromine (MTT). A specific experiment method can refer to: Chem. Eur. J. 2016, 22, 15216-15221.

Human hepatoma cells HepG2 and Huh7 cells and human embryonic kidney cells HEK293 cells are respectively planted on a 96-well plate in a density of $5\times10^3$ per well. The cells are stably grown in the well plate after being incubated for 48 h, and then the copolymer micelles Gal-micelles in Embodiment 7 are respectively added, with concentrations of 0, 10, 25, 50, 100, 150, 200, 400 and 500 μg/mL. After materials and the cells are co-incubated for 48 h, the medium is removed, and washing is carried out for three times with PBS. Then 100 μL of medium containing 0.5 mg/mL MTT without addition of phenol red is added into each well, and then 100 μL of DMSO is added into each well. The absorbance values ($\lambda$=490 nm) of all wells in the 96-well plate that has been developed are detected using a microplate reader. 6 groups of parallel experiments are repeatedly made for each sample, wherein, cell groups which are not acted on by the materials are defined as having 100% cell activity, and wells having only DMSO solution rather than cells are defied as blank control groups for correcting the absorbance value in each well.

Cell survival is calculated as follows:

$$\text{Cell survival rate\%} = (OD_{sample}/OD_{control}) \times 100\%$$

In the formula, $OD_{sample}$ is an absorbance value of an experiment sample group, and $OD_{control}$ is an absorbance value of a cell group which is not acted on by the materials.

Figure 2:
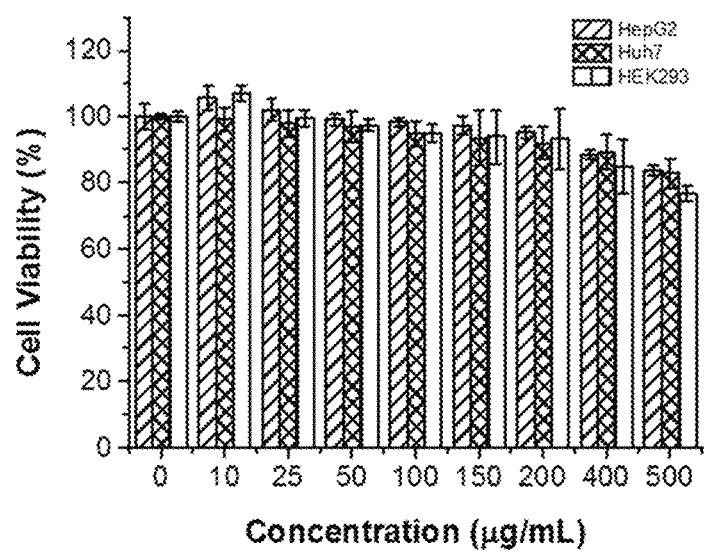
FIG. 2: relative survival rates of human hepatoma cells HepG2 and Huh7 cells and human embryonic kidney cells HEK293 cells after being cultured for 48 h in the presence of different concentrations of copolymer micelles Gal-micelles.

FIG. 2 is a result graph of Gal-micelles cytotoxity, showing that the concentration of copolymer micelle in Embodiment 7 ranges from 0 to 500 μg/mL, and the survival rates of three cells are all more than 80%, which indicates that this copolymer micelle has low toxicity and good biocompatibility.

Similarly, the micelles of the present disclosure prepared in other Embodiments are verified, and the results show that the survival rates of the cells are high, which indicates these micelles are extremely small in toxicity or are non-toxic.

Embodiment 13: the Laser Scanning Confocal Experiment Proves that the Copolymer Micelle Gal-Micelles can Perform Specific Target Recognition on an Asialoglycoprotein Receptor on the Surfaces of Hepatoma Cells HepG2 and Hun7 Cells The blank copolymer micelle Gal-micelles obtained in Embodiment 8 is added to culture solution to carry out cell culture experiment with HEK293 cells, and then cell nucleus is stained with 4',6-diamidino-2-phenyl indole. Through observation under a laser scanning confocal microscope, it can be seen that only a few of Gal-micelles enter HEK293 cells.

Figure 3:
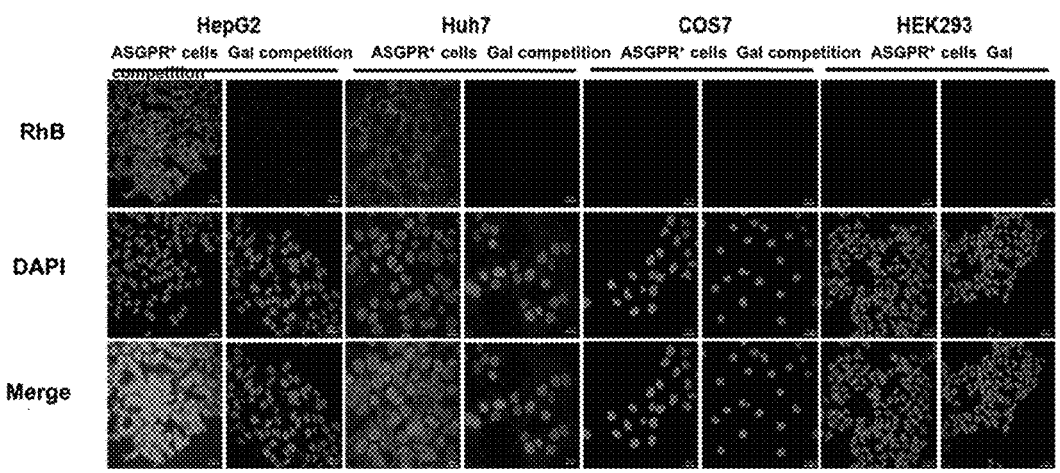
FIG. 3: laser scanning confocal experiment result graphs of human hepatoma cells HepG2 and Huh7 cells and human embryonic kidney cells HEK293 cells after being incubated with copolymer micelle Gal-micelles in the absence or presence of galactose competition.

The blank copolymer micelle Gal-micelles obtained in Embodiment 7 is added into the culture solution to carry out cell culture experiment with HepG2 and Huh7 cells, and then cell nucleus is stained with 4',6-diamidino-2-phenyl indole. The laser scanning confocal microscope experiment results are as shown in FIG. 3, fluorescence of Rhodamine B from the micelle can be clearly observed in the HepG2 和 Huh7 cells, and this fluorescence is almost not observed in COS7 and HEK293 cells. Moreover, under the environment in the presence of galactose competition, the fluorescence of Rhodamine B cannot be observed in HepG2 and Huh7 cells either. This experiment proves that Gal-micelles can be recognized through the galactose-asialoglycoprotein receptor and enter the HepG2 and Huh7 cells.

Embodiment 14: Flow Cytometry Detection Proves that the Copolymer Micelle Gal-Micelles can Perform Specific Target Recognition on Asialoglycoprotein Receptors on the Surfaces of Hepatoma Cells HepG2 and Huh7 Cells In the flow cytometry detection experiment, various cells are cultured in a DMEM medium containing 10% new-born bovine serum (containing 100 U/ml penicillin and 100 μg/mL streptomycin), and are placed in a 37° C., 5% $CO_2$ incubator for growth. Twenty-four hours before transfection, cells at a logarithmic phase are taken, which are digested with 0.02% EDTA and 0.25% trypsin-containing digestive juice and then incubated into a 24-well plate in a density of $5\times10^4$ cells per well. 1 mL of complete culture solution is added into each well, and the culture plate is placed in the incubator to be cultured for 24 h. Wherein, galactose having a final concentration of 1 mmol/L is added in one group to continue to culture for 24 h. Then culture solution is removed when the density of cells in each well reaches 70%, and Gal-micelles nano micelle is added into 490 μL of serum-free and antibiotic-free culture solution to be evenly mixed, and then the mixture is respectively added in different wells. Sample solution in the 24-well plate is sucked after culturing for 5 h at 37° C., and 1 mL of complete medium is added in each well to continue to culture for 20 h. Cells are digested with pancreatin and centrifuged for 3 min at the rotating speed of 1000rpm. Then the supernate is discarded, and gathered cells are resuspended with PBS and then blown off. This centrifugation process is repeated for three times to remove remaining medium and micelle solution, so as to reduce interference on fluorescence detection. Finally, cells are dispersed with PBS and placed in a flow type tube, and fluorescence intensity of cells in each group is detected using a flow cytometry.

In the experiment, HEK293, HepG2 and Huh7 cells are cultured by using two manners, including culturing with a galactose-containing medium (surface receptor is saturated by galactose in advance) and culturing with galactose-free medium (surface asialoglycoprotein receptor is not affected).

After the three types of cells are acted on by the same Gal-micelles nano micelle, the fluorescence intensity of the Rhodamine B molecules in cells is detected using a flow cytometry.

Figure 4:
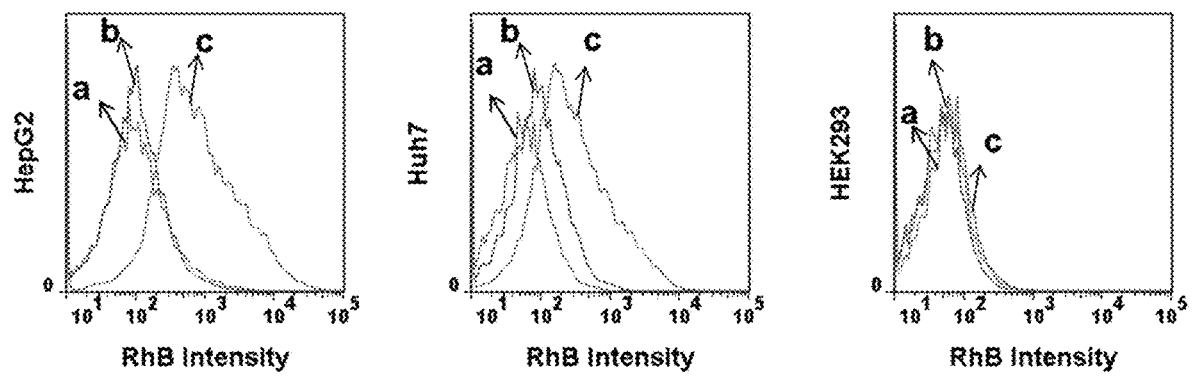
FIG. 4: flow cytometry results of human hepatoma cells HepG2 and Huh7 cells and human embryonic kidney cells HEK293 cells, a) blank control, b) an experimental result that copolymer micelle Gal-micelles is endocytosed by cells in the presence of galactose competition, and c) an experimental result that copolymer micelle Gal-micelles is endocytosed by cells in the absence of galactose competition.

As shown in FIG. 4, for HEK293 cells, under different environments, the speeds of the Gal-micelles nano micelle entering the cells basically have no difference, there has almost no difference compared with the control groups which are not treated by the Gal-micelles nano micelle. It is because there is only the low-expressed asialoglycoprotein receptor on the surfaces of HEK293 cells. Thus, the micelle cannot rapidly enter the cells through surface galactose-asialoglycoprotein receptor targeting mediated endocytosis. However, for HepG2 and Huh7 cells, under different environments, the speeds of Gal-micelles nano micelles entering the cells are distinctly different. Under the condition that surface asialoglycoprotein receptor is saturated in advance, the Gal-micelles nano micelle cannot recognize HepG2 and Huh7 cells through surface-bound galactose, and can only enter tumor cells through non-targeting endocytosis. Thus, the fluorescence intensity of Rhodamine B is extremely low. However, for cells whose surface receptors are over-expressed, Gal-micelles nano micelle can rapidly bind to asialoglycoprotein receptors on the surfaces of the tumor cells through surface-bound galactose, and then enter the tumor cells through receptor mediated endocytosis.

The experiment proves that Gal-micelles nano micelle can perform specific target recognition on the receptors on the surfaces of the HepG2 and Huh7 cells, and are successfully endocytated into cells.

Figure 5:
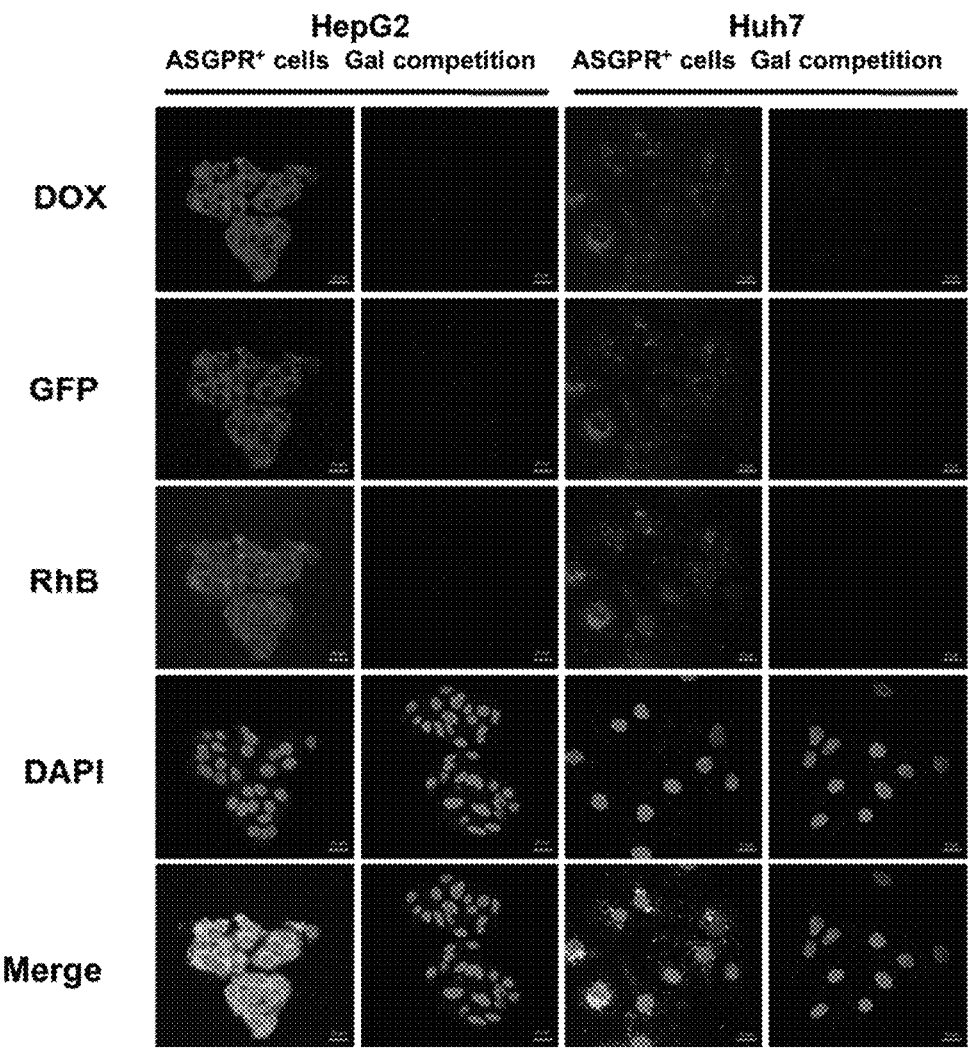
FIG. 5: laser scanning confocal experimental result graphs of human hepatoma cells HepG2 and Huh7 cells and human embryonic kidney cells HEK293 cells after being incubated with drug/gene-loading copolymer micelle DOX@Gal-micelles/pGFP in the absence or presence of galactose competition.

Embodiment 15: Laser scanning confocal microscope pictures prove that gene nucleic acid/drug-loading copolymer micelle DOX@Gal-micelles/pGFP has a strong nucleic acid and drug co-delivery ability The nucleic acid/drug-loading micelle DOX@Gal-micelles/pGFP obtained in Embodiment 10 is added into culture solution to respectively carry out a cell culture experiment with HEK293, HepG2 and Huh7 cells, then cell nucleus is re-stained with 4',6-diamidino-2-phenyl indole. The laser scanning confocal microscope experiment results are as shown in FIG. 5, it can be seen that fluorescence of adriamycin DOX, green fluorescent protein GFP and Rhodamine B in the micelle is obviously present in HepG and Hu7 cells; however, under the environment in the presence of galactose competition, the above three types of fluorescence are almost not observed. The experiment results indicate that DOX@Gal-micelles/pGFP can selectively enter HepG2 and Huh7 cells and can co-deliver drugs and nucleic acid to the two types of cells, and successfully carries out gene transfection.

Embodiment 16: Flow Cytometry Detection Proves that DOX@Gal-Micelles/pGFP Micelle can Perform Target Recognition on Asialoglycoprotein Receptors on the Surfaces of the HepG2 and Huh7 Cells, and Successfully Carries Out Drug Delivery and Bene Transfection In a flow cytometry detection experiment, various cells are cultured in a DMEM medium containing 10% new-born bovine serum (containing 100 U/ml penicillin and 100 µg/mL streptomycin), and are placed in a 37° C., 5% $CO_2$ incubator for growth. Cells at a logarithmic phase are taken 24 h before transfection, are digested with 0.02% EDTA and 0.25% trypsin-containing digestive juice and then incubated into a 24-well plate in a density of $5\times10^4$ cells per well, 1 mL of complete culture solution is added into each well, and a culture plate is placed in the incubator to be cultured for 24 h. Wherein, galactose having a final concentration of 1 mmol/L is added in one group to continue to culture for 24 h, then the culture solution is removed when the density of cells in each well reaches 70%. DOX@Gal-micelles/pGFP nano micelle is added into 490 µL of serum-free and antibiotic-free culture solution to be evenly mixed, and then the mixture is respectively added in different wells. Sample solution in the 24-well plate is sucked after culturing for 5 h at 37° C., and 1 mL of complete medium is added in each well to continue to culture for 20 h. Cells are digested with pancreatin and centrifuged for 3 min at the rotating speed of 1000 rpm. Supernate is discarded, and gathered cells are resuspended with PBS and then blown off. This centrifugation process is repeated for three times to remove remaining medium and micelle solution, so as to reduce interference on fluorescence detection. Finally, cells are dispersed with PBS and placed in a flow type tube, and fluorescence intensity of cells in each group is detected using a flow cytometry.

In the experiment, HEK293, HepG2 and Huh7 cells are cultured by using two manners, including culturing with a galactose-containing medium (surface receptor is saturated by galactose in advance) and culturing with galactose-free medium (surface asialoglycoprotein receptor on the surface is not affected).

Figure 6:
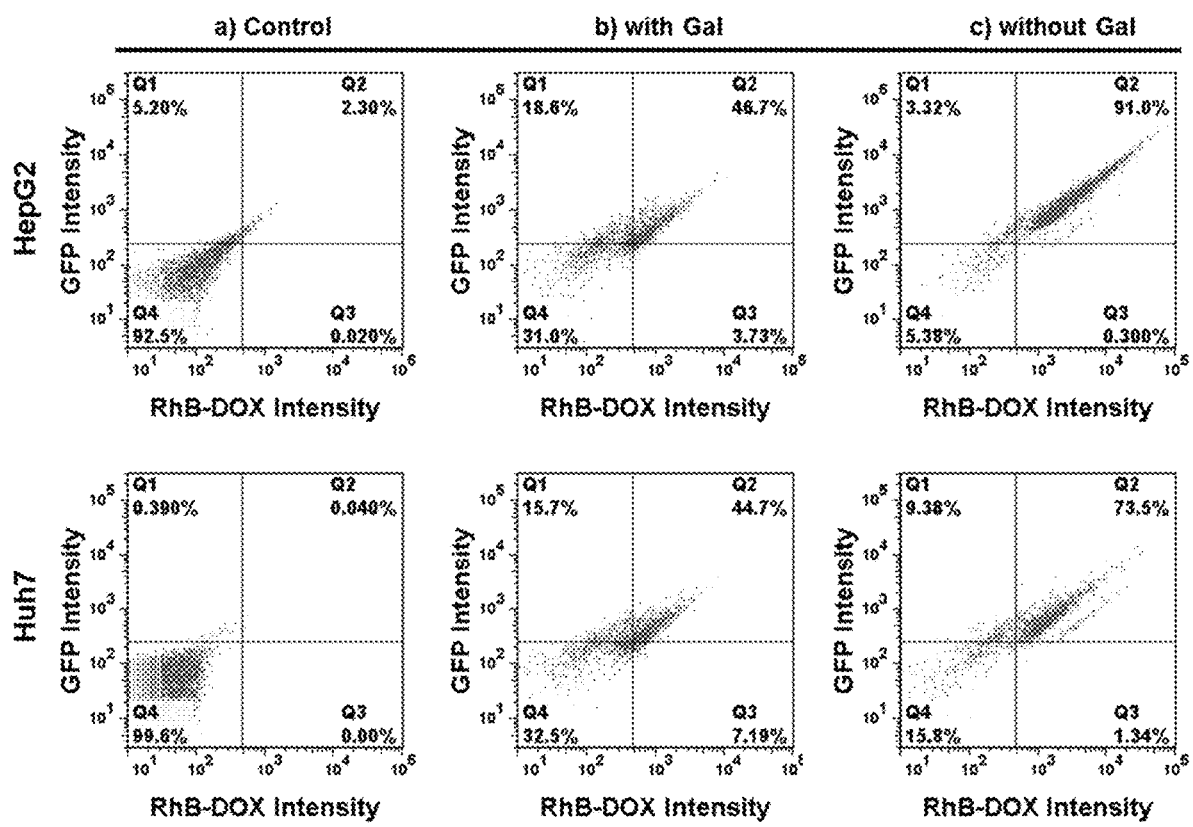
FIG. 6: flow cytometry results of human hepatoma cells HepG2 and Huh7 cells, a) blank control, b) an experimental result that nucleic acid/drug-loading copolymer micelle DOX@Gal-micelles/pGFP is endocytosed by cells in the presence of galactose competition, and c) an experimental result that nucleic acid/drug-loading copolymer micelle DOX@Gal-micelles/pGFP is endocytosed by cells in the absence of galactose competition.

As shown in FIG. 6, after three types of cells are acted on by the same DOX@Gal-micelles/pGFP nano micelle, the fluorescence intensity of different fluorescent molecules in cells is detected using a flow cytometry. The results show that for HEK293 cells, under different environments, the speeds of the DOX@Gal-micelles/pGFP nano micelle entering the cells basically have no difference, there is almost no difference compared with control groups which are not treated by the DOX@Gal-micelles/pGFP nano micelle. It is because there is only low-expressed asialoglycoprotein receptors on the surfaces of HEK293 cells. Thus, the micelle cannot rapidly enter the cells through surface galactose-asialoglycoprotein receptor targeting mediated endocytosis. However, for HepG2 and Huh7 cells, under different environments, the speeds of DOX@Gal-micelles/pGFP nano micelles entering the cells are distinctly different. Under the condition that surface asialoglycoprotein receptor is saturated in advance, the DOX@Gal-micelles/pGFP nano micelles cannot recognize HepG2 cells through surface-bound galactose, and can enter tumor cells only through non-targeting endocytosis. Thus, the fluorescence intensity of Rhodamine B and green fluorescent protein is extremely low. For cells whose surface receptors are over-expressed, DOX@Gal-micelles/pGFP nano micelles can rapidly bind to asialoglycoprotein receptors on the surfaces of the tumor cells through surface-bound galactose, and then enter the tumor cells through receptor-mediated endocytosis, so as to successfully deliver adriamycin and perform gene transfection.

The experiment proves that DOX@Gal-micelles/pGFP nano micelle can perform specific target recognition on the receptors on the surfaces of the HepG2 and Huh7 cells, and can successfully deliver drugs and genes.

Embodiment 17: DOX@Gal-Micelles/siRNA Inhibits Growth of Tumor in a Subcutaneous Solid Tumor Mouse Model For establishment of the subcutaneous solid tumor mouse model, cells are inoculated in right axilla in the density of 0.1 mL $1\times10^8$ cells/mL PBS to the 5-week-old male BALB/c naked mice having the average weight of 15-18 g. Two weeks later, when the size of the tumor exceeds 30 $mm^3$ (volume=0.5×tumor length×tumor $width^2$), mice are divided into 7 groups, with 5 mice in each group. Normal saline, blank copolymer micelle Gal-micelles, adriamycin and Bcl-2 siRNA-loading non-targeting micelle DOX@Glc-micelles/siRNA, adriamycin-loading copolymer micelle DOX@Gal-micelles, Bcl-2 siRNA-loading copolymer micelle Gal-micelles/siRNA, adriamycin and siRNA complex DOX/siRNA, and adriamycin and Bcl-2 siRNA-loading targeting copolymer micelle DOX@Gal-micelles/siRNA are respectively injected, with three doses one week, totally for three weeks. The volume of the tumor tissue is recorded every 2-3 days, and the tumor tissue is isolated from the body and recorded on the last day.

Figure 7:
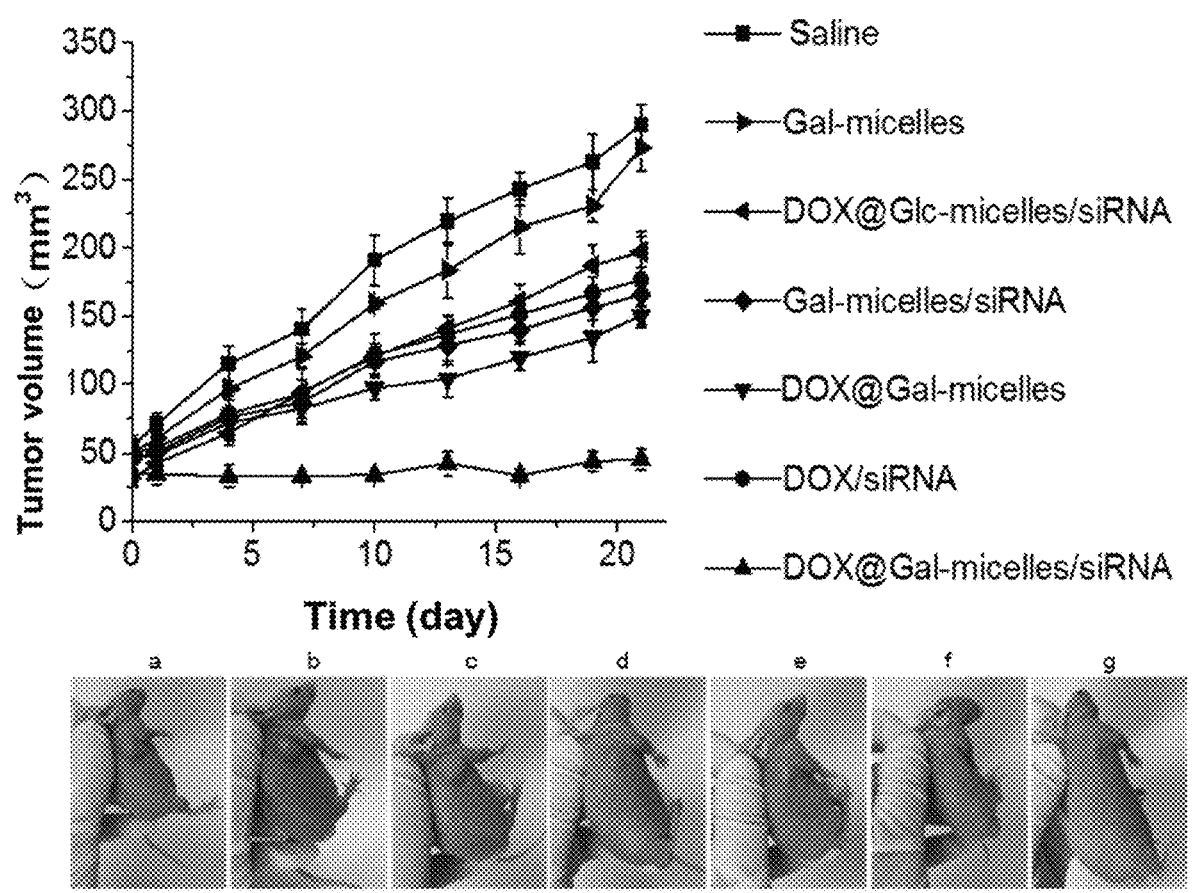
FIG. 7: volume change graphs and final representativeness experiment graphs of subcutaneous solid tumor mice in different treatment groups, wherein the different treatment groups are respectively: a) a normal saline-injected group, b) a blank copolymer micelle Gal-micelles-injected group, c) an adriamycin and Bcl-2 siRNA-loading targeting-free micelle DOX@Glc-micelles/siRNA-injected group, d) an adriamycin-loading copolymer micelle DOX@Gal-micelles-injected group, e) a Bcl-2 siRNA-loading copolymer micelle Gal-micelles/siRNA-injected group, f) an adriamycin and siRNA complex-injected group, and g) an adriamycin and Bcl-2 siRNA-loading target copolymer micelle DOX@Gal-micelles/siRNA-injected group.

As shown in FIG. 7, DOX@Gal-micelles, Gal-micelles/siRNA and DOX@Gal-micelles/siRNA all have the good effect of inhibiting tumor growth, and the inhibition efficiency of the DOX@Gal-micelles/siRNA group is higher than a sum of efficiencies of the single DOX@Gal-micelles group and the single Gal-micelles/siRNA group. According to data of tumor volume of each group obtained on the last experiment day, tumor inhibition efficiency is calculated (tumor inhibition efficiency=(1-average tumor volume of experiment group/average tumor volume of normal saline control group)×100%), the inhibition efficiency of the DOX@Gal-micelles/siRNA group is 84%, and the inhibition efficiencies of DOX@Gal-micelles and Gal-micelles/siRNA are respectively 42% and 40%. It can be concluded that DOX@Gal-micelles/siRNA can maximally inhibit tumor growth.

Embodiment 18: DOX@Gal-Micelles/pGFP Inhibits Growth of Tumor in an In Situ Tumor Mouse Model For establishment of the in situ tumor mouse model, 5-week-old male BALB/c naked mice having the average weight of 15-18 g are taken, and their abdomens are cut to expose liver lobes, and left outer lobes of livers are squeezed out. Cells are inoculated in right axilla in the density of 0.1 mL $1\times10^8$ cells/mL PBS, and suturing is carried out to close the abdomens. Two weeks later, mice are divided into 7 groups, with 5 mice in each group. Normal saline, blank copolymer micelle Gal-micelles, adriamycin and Bcl-2 siRNA-loading non-targeting micelle DOX@Glc-micelles/siRNA, adriamycin-loading copolymer micelle DOX@Gal-micelles, Bcl-2 siRNA-loading copolymer micelle Gal-micelles/siRNA, adriamycin and siRNA complex, and adriamycin and Bcl-2 siRNA-loading targeting copolymer micelle DOX@Gal-micelles/siRNA are respectively injected, with three-time doses one week, totally for three weeks. On the last day, the liver tissue is isolated from the body to observe the metastasis of cancer cells in liver, and the number and volumes of the tumors in liver are recorded.

Figure 8:
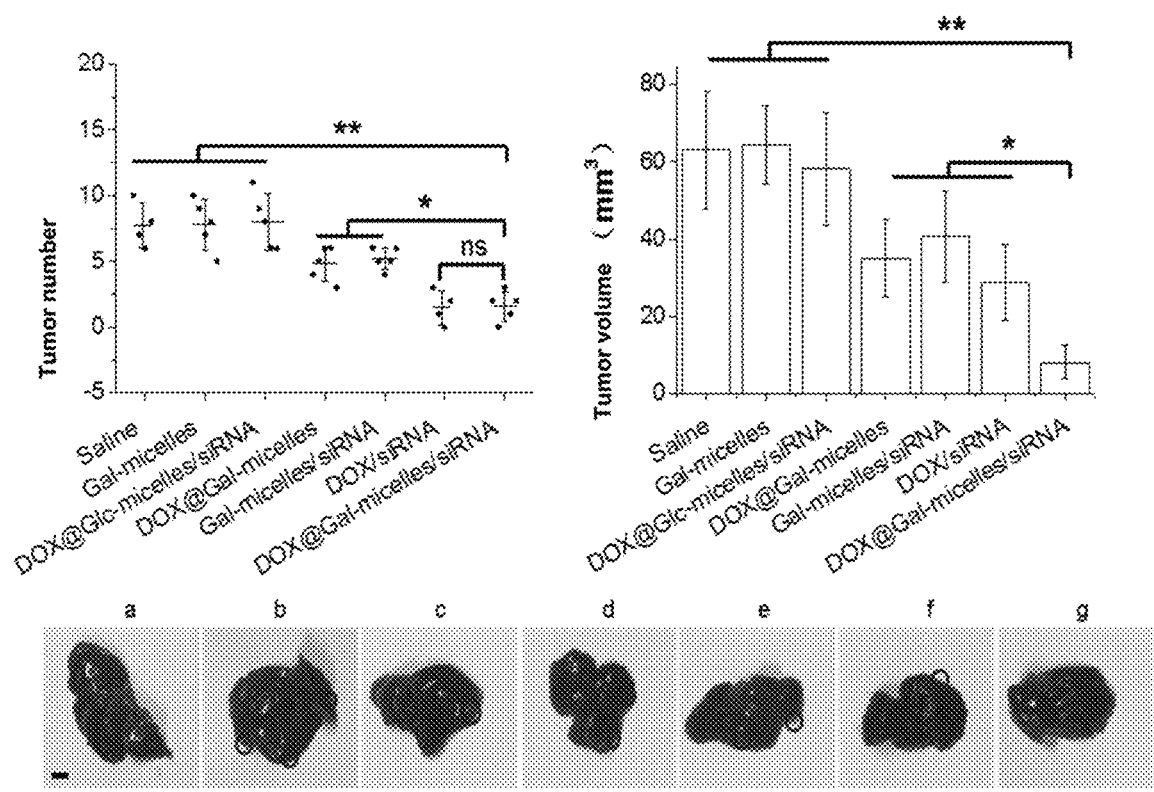
FIG. 8: final tumor number and volume and final representativeness experiment graphs of in situ mice in different treatment groups, wherein the different treatment groups are respectively: a) a normal saline-injected group, b) a blank copolymer micelle Gal-micelles-injected group, c) an adriamycin and Bcl-2 siRNA-loading targeting-free micelle DOX@Glc-micelles/siRNA-injected group, d) an adriamycin-loading copolymer micelle DOX@Gal-micelles-injected group, e) a Bcl-2 siRNA-loading copolymer micelle Gal-micelles/siRNA-injected group, f) an adriamycin and siRNA complex-injected group, and g) an adriamycin and Bcl-2 siRNA-loading target copolymer micelle DOX@Gal-micelles/siRNA-injected group.

As shown in FIG. 8, the DOX@Gal-micelles/siRNA group has the minimum tumor number and the most smallest tumor volume among all the experiment groups, and has the highest tumor growth inhibition efficiency.

What is claimed is:

1. A liver-targeting pH-sensitive tracing copolymer nano micelle system, comprising a copolymer formed by monomer N,N-dimethylaminoethyl methacrylate DMAEMA having pH sensitivity and hydrophobic monomer 3-azido-2-hydroxypropyl methacrylate PGMA-N3, wherein one end of the copolymer is modified with a fluorescent molecule having a fluorescence tracing function, and the other end is modified with galactose or galactosamine.

2. The liver-targeting pH-sensitive tracing copolymer nano micelle system according to claim 1, capable of loading nucleic acid for gene therapy, or drug for chemotherapy.

3. The liver-targeting pH-sensitive tracing copolymer nano micelle system according to claim 1, wherein the copolymer has a structural formula as shown in Formula 1:

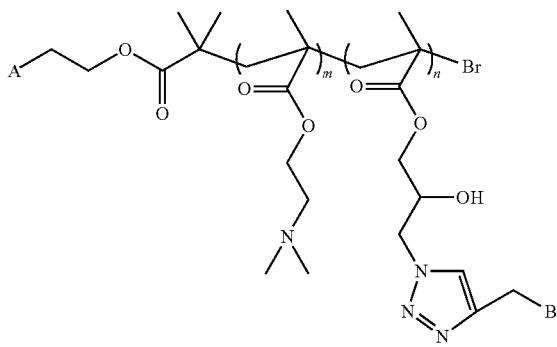

Formula 1 wherein A is one or more identical or different fluorescent molecules having a fluorescence tracing function selected from Rhodamine B, fluorescein isothiocyanate and BODIPY; wherein m and n are each integers representing the degree of polymerization.

4. The liver-targeting pH-sensitive tracing copolymer nano micelle according to claim 3, wherein the copolymer has a structural formula as shown in Formula 1:

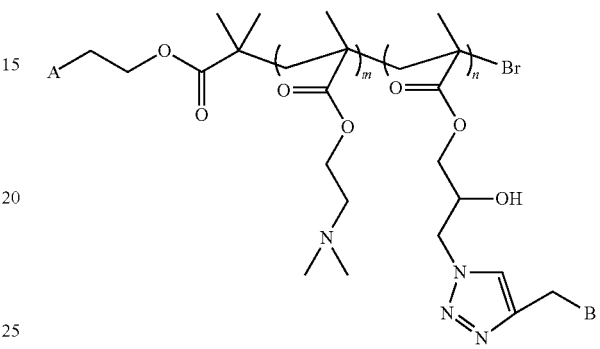

Formula 1 wherein A is one or more identical or different fluorescent molecules having a fluorescence tracing function selected from Rhodamine B, fluorescein isothiocyanate and BODIPY.

5. The liver-targeting pH-sensitive tracing copolymer nano micelle system according to claim 3, wherein m is 25, and n is 50; and the fluorescent molecule is Rhodamine B, the mole ratio of Rhodamine B to DMAEMA to GMA-N3 is 1:25:50, and the ratio of galactose or galactosamine to GMA-N3 is 1:1.

6. The liver-targeting pH-sensitive tracing copolymer nano micelle system according to claim 2, wherein the drug for chemotherapy is a hydrophobic anti-cancer drug and an anti-tumor drug.

7. The liver-targeting pH-sensitive tracing copolymer nano micelle system according to claim 2, wherein the nucleic acid for gene therapy comprises plasmid DNA or small molecule siRNA.

8. The liver-targeting pH-sensitive tracing copolymer nano micelle system according to claim 1, wherein the average particle size of the nano micelle is 155 nanometer.

9. The liver-targeting pH-sensitive tracing copolymer nano micelle system according to claim 2, wherein the average particle size of the nano micelle is 155 nanometer.

* * * * *